(12) United States Patent
Pinkos et al.

(10) Patent No.: US 9,975,829 B2
(45) Date of Patent: May 22, 2018

(54) METHOD FOR THE PREPARATION OF 1,4-BUTANE DIOL HAVING AN APHA COLOR INDEX OF LESS THAN 30

(71) Applicant: BASF SE, Ludwigshafen (DE)

(72) Inventors: Rolf Pinkos, Bad Duerkheim (DE); Olga Osetska, Mannheim (DE); Irene de Wispelaere, Mannheim (DE); Stefan Dudenhoeffer, Ludwigshafen (DE); Christina Walczuch, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 212 days.

(21) Appl. No.: 15/030,627

(22) PCT Filed: Oct. 13, 2014

(86) PCT No.: PCT/EP2014/071886
§ 371 (c)(1),
(2) Date: Apr. 20, 2016

(87) PCT Pub. No.: WO2015/058990
PCT Pub. Date: Apr. 30, 2015

(65) Prior Publication Data
US 2016/0244387 A1    Aug. 25, 2016

(30) Foreign Application Priority Data
Oct. 23, 2013    (EP) .................................... 13189864

(51) Int. Cl.
*B01D 3/34* (2006.01)
*C07C 29/80* (2006.01)
*C07C 29/88* (2006.01)
*B01D 3/14* (2006.01)
*C07C 29/94* (2006.01)

(52) U.S. Cl.
CPC .............. *C07C 29/80* (2013.01); *B01D 3/141* (2013.01); *B01D 3/34* (2013.01); *C07C 29/88* (2013.01); *C07C 29/94* (2013.01)

(58) Field of Classification Search
CPC .......... B01D 3/141; B01D 3/34; C07C 29/80; C07C 29/88; C07C 29/94
See application file for complete search history.

(56) References Cited

U.S. PATENT DOCUMENTS

| 4,032,583 | A |   | 6/1977 | Arganbright et al. |
|---|---|---|---|---|
| 4,154,970 | A | * | 5/1979 | Beer ....................... C07C 29/74 568/868 |
| 5,209,825 | A |   | 5/1993 | Badat et al. |
| 5,945,571 | A | * | 8/1999 | Pinkos .................. C07C 29/132 568/865 |
| 2003/0018224 | A1 |   | 1/2003 | Tsuji et al. |
| 2014/0116872 | A1 |   | 5/2014 | Izawa et al. |
| 2014/0135511 | A1 |   | 5/2014 | Izawa et al. |

FOREIGN PATENT DOCUMENTS

| CA | 2226534 A1 | 7/1998 |
|---|---|---|
| DE | 19801089 A1 | 7/1998 |
| EP | 0000159 A1 | 1/1979 |
| JP | S61197534 A | 9/1986 |
| JP | H07258129 A | 10/1995 |
| WO | WO-2013/005748 A1 | 1/2013 |
| WO | WO-2013/012047 A1 | 1/2013 |

OTHER PUBLICATIONS

International Search Report for International Patent Application No. PCT/EP2014/071886, dated Jan. 8, 2015.

* cited by examiner

*Primary Examiner* — In Suk C Bullock
*Assistant Examiner* — Gabriel E Gitman
(74) *Attorney, Agent, or Firm* — Marshall, Gerstein & Borun LLP

(57) ABSTRACT

Method for preparing 1,4-butanediol having an APHA color index of less than 30 by treating substance mixtures comprising 1,4-butanediol by distillation of the 1,4-butanediol in the presence of complex hydrides.

7 Claims, No Drawings

METHOD FOR THE PREPARATION OF 1,4-BUTANE DIOL HAVING AN APHA COLOR INDEX OF LESS THAN 30

CROSS-REFERENCE TO RELATED APPLICATIONS

This is the U.S. national phase of International Application No. PCT/EP2014/071886, filed Oct. 13, 2014, which claims the benefit of European Patent Application No. 13189864.5, filed Oct. 23, 2013.

The invention relates to a purification process for preparing 1,4-butanediol having an APHA color index of less than 30 by distillation of the 1,4-butanediol in the presence of complex hydrides.

PRIOR ART 1,4-Butanediol may be prepared by various routes. Some variants are described in WO/2013/012047 A1 and WO/2013/005748, for example based on diacetoxybutene, propene, 1,4-butynediol, carboxylic acid derivatives such as maleic anhydride or succinic acid and also direct fermentation to butanediol.

WO/2013/012047 A1 describes the hydrogenation of C4-containing unsaturated starting materials in the presence of butanediol and low amounts of amines on solid catalysts with elements of the 9th-11th group of the periodic table of the elements. Since amines and unsaturated C4 components are not the only secondary components in butanediol-containing material streams but rather also comprise to a greater or lesser extent, depending on the process, sulfur-containing and other components which can be hydrogenated such as aldehydes, hemiacetals, acetals or ketones, esters and acids and also anions and cations, it is questionable whether the aforementioned method is generally readily applicable.

Finally, for economic reasons, the longest possible catalyst service life is desirable. As is known, sulfur compounds are especially pronounced catalyst poisons, acids and esters in the presence of water can attack the catalysts such that their support structure is destroyed, and aldehydes can split off CO which negatively influences the activity of catalysts. Therefore, an initially well-functioning process becomes increasingly more inefficient. This can be observed, for example, in the increase in non-hydrogenated products, which then negatively influences the color index or the color index stability of the desired end product, for example.

OBJECTIVE

Accordingly, a method was sought which can be operated reliably and cost-effectively over a long time period, even in the presence of one or more of the components harmful to catalysts mentioned above.

DESCRIPTION OF THE INVENTION

The invention relates to a method for preparing 1,4-butanediol having an APHA color index of less than 30 by treating substance mixtures comprising 1,4-butanediol by distillation of the 1,4-butanediol in the presence of complex hydrides.

The 1,4-butanediol thus obtained has high purities and low APHA color indices, in particular APHA color indices of less than 30, preferably less than 15, particularly preferably less than 10, 9, 8, 7, 6, 5, 4, 3 and 2, and additionally a high color index stability which means that the APHA color index of the product does not notably increase even on storage.

Complex hydrides are those specified, for example, in Advanced Organic Chemistry, J. March, 4th edition J. Wiley & Sons, 1992, pages 910-917. For instance, $BH_3$, $AlH_3$, $LiBH_4$, $NaBH_4$, $KBH_4$, $LiAlH_4$, $NaAlH_4$, $KAlH_4$, the aforementioned forms in which some of the hydridic hydrogens are replaced by formal anions such as alkylate, alkoxylate, acylate and the like can and also Si hydrides such as $Et_3SiH$ for example.

The hydrides may comprise additives such as alkali metal hydroxides or alkaline earth metal hydroxides such as Li, La and Ce salts in the form of halides, sulfates, phosphates or carboxylates.

Particular preference is given to sodium borohydride, for example in the form of Borol™, and lithium aluminum hydride. Very particular preference is given to $NaBH_4$, in the form of alkaline aqueous solutions for example, as are sold under the name "Borol™ solution" by Rohm and Haas or under the name "VenPure™ solution" by Dow Chemical Company. These are in the form of an aqueous solution of 25-40% by weight NaOH and 10-12.5% by weight $NaBH_4$.

The complex hydrides are used, for example, in amounts between 1 and 50 000 ppm, preferably from 50 to 25 000 ppm, particularly preferably between 100 and 10 000 ppm, based on the amount of butanediol to be purified.

After addition of the complex hydrides, the solution has a pH of 4 to 14 if a water content of >10% is present. The pH is preferably between 5 and 12, especially preferably between 6 and 10. If the water content in the butanediol-containing stream to be purified is below 10%, the mixture can be diluted with water for the pH measurement.

The complex hydrides can be introduced in the absence of solvent or in solution or as a suspension. The solvent used should be one which does not generate any hydrogen, or only generates a small amount, with the hydride. Preference is given to water, the butanediol to be purified, and ethers such as tetrahydrofuran and diethyl ether. Particular preference is given to water, which may in addition comprise alkali metal hydroxides such as NaOH, or as ready-prepared Borol™ solution.

The complex hydride, which is added to the butanediol to be purified, can be added at temperatures between 10 and 250° C., preferably between 20 and 170° C., particularly preferably between 35 and 100° C., depending on the site of addition.

If the complex hydride is added to the substance mixture comprising butanediol to be purified before the at least one distillation column, the mean residence time in the container before the column is at least 0.1 h. Preference is given to 0.5 h, particular preference being given to 1 h.

The following discusses the distillation generally, in order then to subsequently illustrate where and how the hydrides can be added.

The starting material with the substance mixtures comprising butanediol, which is also referred to as crude butanediol, in addition to 1,4-butanediol generally also comprises low and high boilers, which must be very substantially removed. By way of example, low boilers are, depending on the method, water, methanol, ethanol, propanol, butanol, acetic acid, acetates, formaldehyde acetals, gamma-butyrolactone, acetaldehyde, acetaldehyde acetals, e.g. that with 1,4-butanediol, other esters, ketones, N-containing compounds, 4-hydroxybutyraldehyde, isomeric butanediols, ethylene glycol, 1,2- or 1,3-propylene glycol and THF.

By way of example, high boilers are, depending on the preparation process, pentanediol and hexanediols, dimeric butanediol, esters of butanediol and gamma-butyrolactone, hydroxycarboxylic acids such as lactic acid or malic acid, succinic acid or esters thereof, glycerol, amino acids, amides, carbohydrates and derivatives or degradation products of carbohydrates.

The work-up results therefrom by means of distillation in at least one column. Here, preference is given to a continuous work-up. If only one column is actually used, low boilers are obtained, at least in part, via the top fraction, high boilers via the bottoms and butanediol as a side draw (gas or liquid takeoff).

In a particularly suitable embodiment, a so-called dividing wall column is used in this case. Depending on the content and the nature of the components to be separated from butanediol, it is usually advantageous to use two or more columns. If water is present as a significant constituent of the low boilers, this is removed, together optionally with other low boilers, in at least one column at pressures of 0.05 to 5 bar and bottom temperatures between 80 and 200° C.

If a lot of water is present, for example, more than 40% by weight %-fraction of the butanediol-containing mixture, it can be advantageous to remove the water in at least two columns, wherein the first column is operated at relatively high pressures, for example between 1 and 5 bar absolute, and then the second at lower pressures, for example at 100-1000 mbar absolute.

In an optional second column, pure butanediol is then separated from high boilers, wherein butanediol is obtained here via the top fraction or as a side draw, optionally in a dividing wall column.

In a further preferred embodiment, the complex hydrides are added to the butanediol to be processed, freed by distillation from low boilers such as water and the butanediol comprising hydride is separated into high boilers, which comprise the hydride, and butanediol via a simple evaporation. The butanediol can then be further purified by distillation as described above. The evaporation is carried out, for example, in a thin film evaporator (Sambay® evaporator), a falling film evaporator or other evaporators known to those skilled in the art.

Should only a small amount of butanediol be purified, this is also possible by batchwise distillation. Depending on requirements, a combination of batchwise and continuous distillation is also possible. In the batchwise distillation, the low boilers are generally distilled off initially, then the butanediol. The high boilers remain in the bottoms and are subsequently disposed of. The low boilers are generally distilled off at a higher pressure than butanediol. For example, water and other low boilers are distilled off at ambient pressure. As soon as the distillation output falls, the pressure is decreased continuously and/or the temperature in the bottoms is increased continuously. For instance, pure butanediol then distills off at pressures about 45 mbar absolute and bottom temperatures of ca. 152° C.

The distillations are advantageously carried out in columns with separation-enhancing internals, especially in the pure distillation of the butanediol. These internals should correspond to a number of theoretical plates of at least 5, being preferably 10, particularly preferably 15. The internals may be, for example, a loose bed of random packings composed of metal, ceramic or teflon, valve trays, bubble trays or structured packings such as are commercially available.

For optimal performance of the method according to the invention, it is important that the distillations, especially the pure distillation of butanediol, are conducted largely with the exclusion of air. Here, the molar ratio of oxygen to 1,4-butanediol is less than 1:100, preferably less than 1:1000, particularly preferably less than 1:10 000. To avoid oxygen, it is recommended to use columns that are as dense as possible. If too much oxygen is present, firstly the purity target of the butanediol can be missed, by oxidation reactions for example, and secondly increased color indices must be taken into account. Furthermore, oxygen can impair the effect of the hydrides or as a result of oxidation of the hydrides may generate deposits in the columns and evaporators which would necessitate laborious cleaning of the columns.

The lower the distillation pressure, the more attention must be paid to the gas-tightness of the distillation apparatus used. Increased gas-tightness in columns is achieved e.g. by weld lip sealing, seals with grooved profiles, by using particularly smooth sealing surfaces, by avoiding multiple flanges or access points in the columns such as, for example, for measuring pressure and temperature, or sight glasses and so forth.

A further possibility for avoiding oxygen is to provide the distillation unit with an external jacket which is inertized by means of nitrogen or argon, for example. Furthermore, flanges can also be welded.

A possibility for measuring oxygen consists in capturing the offgas from the vacuum unit and analyzing the composition of the gas mixture obtained. Evidence of the oxygen input into the column is best obtained in this case by operating the column under the preferred conditions but without intake.

The complex hydrides may be used already prior to the low boiler removal or else thereafter. It is possible, for example, to use NaBH4 in the form of molded bodies, over which the butanediol-containing stream is passed, partly or completely, at temperatures of 10-80° C. The product stream partly takes up the hydride in dissolved form and thus reaches the distillation. The hydride can however also be mixed as a powder with the product stream such that it is present in the distillation as a homogeneous mixture. Furthermore, the hydride may be dissolved separately in a solvent such as water or methanol or THF and be fed to the butanediol-containing stream as a homogeneous solution. In this case, a preferred embodiment is the feeding of Borol™, a commercially available product, as a mixture of NaBH4, water and NaOH.

Preferred sites at which the complex hydride can be introduced into the process are the low boiler-containing feed, the bottoms of the low-boiler separation column, the feed of the butanediol purification column and the bottoms of the butanediol purification column. Particular preference is given to the low boiler-containing feed or the feed to the butanediol purification column.

A special feature of the method is the handling of the hydride-containing bottom product of the butanediol purification column. At bottoms temperatures of 130-230° C., preferably 150-190° C., the residual butanediol content in the bottoms is adjusted to 1-90% by weight, preferably 5-70% by weight, particularly preferably 10-50% by weight. After cooling the bottoms to below 100° C., this is admixed with water. For this purpose, the low boiler product, or a partial stream thereof, is preferably used. If the dilution is not carried out, there is a risk of the precipitation of a solid. The degree of dilution at least 1 part water to 2 parts bottoms, preferably at least 1:1, particularly preferably at least 2:1.

If it is desired to eliminate residual hydride, the bottoms may be acidified. For this purpose, all acids in principle are possible, preferably those which mix with the bottoms optionally admixed with water, such as (optionally diluted with water) formic acid, acetic acid, sulfuric acid or hydrochloric acid.

The butanediol prepared by the method according to the invention has particularly high purities and also has a stable color index over long periods. The purity is as usual determined by gas chromatography and is above 99%, preferably above 99.6%, particularly preferably above 99.8%.

A further characteristic of the method according to the invention is the low content of 4-hydroxy-1-butoxy-THF in the distilled butanediol. This is generally below 3000 ppm, preferably below 1500 ppm, particularly preferably below 800 ppm.

The color indices (APHA Hazen Color index) are below 30 APHA, preferably below 20 APHA, particularly preferably below 10 APHA. The APHA color index is a test method issued by the American Public Health Association (APHA) for color measurement in liquids. A cobalt platinate solution is used as calibration standard according to ISO 6271. The APHA color index can easily be measured in specific photometers, e.g. those from Chemtronic Waltemode GmbH.

In the following, acetal signifies 4-hydroxy-1-butoxy-THF.

All distillations were carried out in a batch column. The column had a diameter of ca. 2.7 cm and had been filled with 3-5 mm Raschig rings along a length of 80 cm. A reflux divider was located at the top of the column, which was adjusted so that 1 part distillate was drawn off and 2 parts distillate were recycled into the column.

The method according to the invention allows the preparation of highly purified 1,4-butanediol having an APHA color index of less than 30. Furthermore, this 1,4-butanediol thus prepared is stable on storage, i.e. even on storage for more than 24 hours for example at elevated temperature (50° C.), the APHA color index does not notably increase.

EXPERIMENTAL SECTION

Example 1

In a 1 liter round-bottomed flask, 750 g of crude butanediol were initially charged, which comprised, in addition to ca. 49% 1,4-butanediol, ca. 45% water, ca. 0.3% gamma-butyrolactone, 0.15% acetal, 0.05% 4-hydroxybutyraldehyde, ca. 1% methanol, ca. 1.1% propanol, ca. 1.3% n-butanol, ca. 0.1% formaldehyde acetals and hemiacetals, ca. 0.1% 2-methyl-1,4-butanediol and also some partly unknown high and low boilers. The mixture had a color index of 175 APHA and a pH of 7.1. 5 g of a Borol™ solution (Dow Chemicals, VenPlus Solution) were added under an inert gas (nitrogen). ca. 94 g of low boilers, initially at 500 mbar, then at 100 mbar and bottom temperatures of 112-134° C. were distilled off from the mixture. After change of the fraction, the bottom temperature was increased to ca. 150° C., and at 50 mbar ca. 65 g of intermediate fraction (ca. 32% water, content by GC, calculated as anhydrous, of butanediol: 98.1%, color index 6 APHA) were distilled off. Subsequently, at ca. 40 mbar, ca. 520 g of main fraction were distilled off at ca. 150° C. The 1,4-butanediol from the main fraction had a purity by GC of 99.85%, 2-methylbutanediol 0.092%, acetal content was 0.077%, gamma-butyrolactone was undetectable. The color index was 8 APHA. The sample was filled into a sheet metal can (material 1.0425) and stored at 50° C. After 24 h, the color index was unchanged at 8 APHA.

Comparative Example 1

Example 1 was repeated but without the addition of Borol™. After removal of the main amount of low boilers and water, ca. 85 g of intermediate fraction were obtained (color index 7 APHA, water content ca. 80%, content by GC, calculated as anhydrous, of butanediol: ca. 60%). ca. 4 g were obtained as main fraction. The 1,4-butanediol from the main fraction had a purity by GC of 99.54%, 2-methylbutanediol 0.095%, acetal content was 0.219%, gamma-butyrolactone 0.014%. The color index was 6 APHA. The sample was filled into a sheet metal can (material 1.0425) and stored at 50° C. After 24 h, the color index was 35 APHA.

Example 2

In a 1 liter round-bottomed flask, 750 g of crude butanediol were initially charged, which comprised, in addition to ca. 84% 1,4-butanediol, ca. 15% water, ca. 0.01% gamma-butyrolactone, ca. 0.15% acetal, 0.01% acetaldehyde and acetal and hemiacetal thereof with butanediol and also some further unknown high and low boilers. The mixture had a color index of 75 APHA and a pH of 9. 5 g of a Borol™ solution (Dow Chemicals, VenPlus Solution) were added under an inert gas (nitrogen). ca. 94 g of low boilers, initially at 500 mbar, then at 100 mbar and bottom temperatures of 112-134° C. were distilled off from the mixture. After change of the fraction, the bottom temperature was increased to ca. 150° C., and at 50 mbar ca. 65 g of intermediate fraction (ca. 32% water, content by GC, calculated as anhydrous, of butanediol: 98.1%, color index 6 APHA) were distilled off. Subsequently, at ca. 40 mbar, ca. 520 g of main fraction were distilled off at ca. 150° C. The 1,4-butanediol from the main fraction had a purity by GC of 99.895%, acetal content was 0.071%, gamma-butyrolactone was undetectable. The color index was 6 APHA. The sample was filled into a sheet metal can (material 1.0425) and maintained at a temperature of 50° C. After 24 h, the color index was unchanged at 6 APHA.

Comparative Example 2

Example 2 was repeated but without the addition of Borol™ (pH of ca. 6.5). After removal of the main amount of water, ca. 78 g of intermediate fraction were obtained (color index 15 APHA, water content ca. 39%, content by GC, calculated as anhydrous, of butanediol: 97.5%). ca. 529 g were obtained as main fraction. The 1,4-butanediol from the main fraction had a purity by GC of 99.693%, acetal content was 0.175%, gamma-butyrolactone 0.014%. The color index was 6 APHA. The sample was filled into a sheet metal can (material 1.0425) and maintained at a temperature of 50° C. After 24 h, the color index was 51 APHA.

Example 3

In a 1 liter round-bottomed flask, 750 g of crude butanediol were initially charged, which comprised, in addition to ca. 98% 1,4-butanediol, ca. 0.5% water, ca. 0.5% gamma-butyrolactone, 0.13% acetal and also some further unknown high and low boilers. The mixture had a color index of 25 APHA. 0.5 g of LiAlH4 was added under inert gas (nitrogen). At a bottom temperature of ca. 150° C. and 50 mbar, ca. 50 g were distilled off from the mixture. This fraction comprised ca. 8% water, content by GC, calculated as anhydrous, of butanediol 93.2%, color index 8 APHA). Subsequently, at ca. 40 mbar, ca. 620 g of main fraction were distilled off at ca. 150° C. The 1,4-butanediol from the main fraction had a purity by GC of 99.912%, acetal content was 0.054%, gamma-butyrolactone was undetectable. The color index was 5 APHA. The sample was filled into a sheet metal can (material 1.0425) and heated to 50° C. After 24 h, the color index was unchanged at 5 APHA.

Comparative Example 3

Example 3 was repeated but without the addition of LiAlH4. As first fraction, ca. 45 g were obtained (color index 9 APHA, water content ca. 9%, content by GC, calculated as anhydrous, of butanediol: 92.5%). ca. 623 g were obtained as main fraction. The 1,4-butanediol from the main fraction had a purity by GC of 99.731%, acetal content was 0.151%, gamma-butyrolactone 0.024%. The color index was 6 APHA. The sample was filled into a sheet metal can. After 24 h, the color index was 12 APHA.

The invention claimed is:

1. A method for preparing 1,4-butanediol having an APHA color index of less than 30 comprising treating a substance mixture comprising 1,4-butanediol by distillation of the 1,4-butanediol in the presence of a complex hydride.

2. The method according to claim 1, wherein the complex hydride used is $NaBH_4$.

3. The method according to claim 2, wherein $NaBH_4$ is used as an aqueous alkaline solution.

4. The method according to claim 1, wherein the distillation of the 1,4-butanediol is operated continuously.

5. The method according to claim 4, wherein the distillation is operated using a dividing wall column.

6. The method according to claim 1, wherein the pH of the mixture of substance mixture comprising 1,4-butanediol and hydride has a pH of 4 to 14 at a minimum water content of 10%.

7. The method according to claim 2, wherein the pH of the mixture of substance mixture comprising 1,4-butanediol and hydride has a pH of 4 to 14 at a minimum water content of 10%.

* * * * *